United States Patent
Weber

(10) Patent No.: US 9,804,074 B2
(45) Date of Patent: Oct. 31, 2017

(54) METHOD AND SYSTEM FOR RESISTIVE-TYPE PARTICULATE MATTER SENSORS

(71) Applicant: Ford Global Technologies, LLC, Dearborn, MI (US)

(72) Inventor: David Charles Weber, Toledo, OH (US)

(73) Assignee: Ford Global Technologies, LLC, Dearborn, MI (US)

( * ) Notice: Subject to any disclaimer, the term of this patent is extended or adjusted under 35 U.S.C. 154(b) by 280 days.

(21) Appl. No.: 14/702,566

(22) Filed: May 1, 2015

(65) Prior Publication Data

US 2016/0320285 A1    Nov. 3, 2016

(51) Int. Cl.
*G01N 15/06* (2006.01)
*B01D 53/94* (2006.01)
(Continued)

(52) U.S. Cl.
CPC ..... *G01N 15/0656* (2013.01); *B01D 53/9422* (2013.01); *F01N 3/021* (2013.01); *F01N 3/0842* (2013.01); *F01N 3/0885* (2013.01); *F01N 13/0097* (2014.06); *F02D 41/028* (2013.01); *F02D 41/1466* (2013.01); *F02D 41/20* (2013.01); *F02D 41/222* (2013.01); *G01N 15/0606* (2013.01); *B01D 53/9477* (2013.01); *B01D 53/9495* (2013.01); *B01D 2255/2042* (2013.01); *F01N 2560/05* (2013.01); *F01N 2560/20* (2013.01); *G01N 2015/0046* (2013.01); *Y02T 10/24* (2013.01)

(58) Field of Classification Search
CPC ............ F02D 41/1466; F02D 41/1494; G01M 15/102; F01N 3/0885; F01N 2560/05; G01N 15/0606; G01N 15/0656
See application file for complete search history.

(56) References Cited

U.S. PATENT DOCUMENTS 4,719,441 A    1/1988  Horn
5,637,786 A *  6/1997  Weber ................ G01N 27/4067
                                                  123/697

(Continued)

OTHER PUBLICATIONS

Al Kharafi, F.M. et al., "Electrochemical Oxidation of Sulfide Ions on Platinum Electrodes," Modern Applied Science, vol. 4 No. 3, Mar. 2010, 10 pages.

*Primary Examiner* — Justin Olamit
(74) *Attorney, Agent, or Firm* — Julia Voutyras; McCoy Russell LLP

(57) ABSTRACT

Methods and systems are provided for reducing soot sensor electrode degradation in harsh chemical environment introduced as a result of desulfation of a lean NOx trap positioned upstream of the soot sensor. In one example, a method may include in response to the SOx load being higher than the threshold, prior to initiating desulfation of LNT, operating the soot sensor in a pre-desulfation mode where the negative electrode is connected to the positive electrode for a brief duration, while the positive electrode is disconnected from the positive electrode. However during desulfation, when $H_2S$ is released as a by-product, both the electrodes may be open, i.e. not connected to the positive electrode or ground, thereby reducing the possibility of sensor degradation.

19 Claims, 7 Drawing Sheets

(51) Int. Cl.

| | |
|---|---|
| *F01N 3/08* | (2006.01) |
| *F02D 41/02* | (2006.01) |
| *F02D 41/14* | (2006.01) |
| *F02D 41/20* | (2006.01) |
| *F02D 41/22* | (2006.01) |
| *F01N 3/021* | (2006.01) |
| *F01N 13/00* | (2010.01) |
| *G01N 15/00* | (2006.01) |

(56) References Cited

U.S. PATENT DOCUMENTS

| | | | |
|---|---|---|---|
| 7,543,477 B2 | 6/2009 | Berger et al. | |
| 8,578,756 B2* | 11/2013 | Suzuki | G01K 7/16 |
| | | | 73/23.31 |
| 8,823,401 B2* | 9/2014 | Roth | G01N 15/0656 |
| | | | 324/699 |
| 9,145,814 B2* | 9/2015 | Lee | F01N 9/002 |
| 9,217,349 B2* | 12/2015 | Hashida | G01N 15/0656 |
| 9,389,163 B2* | 7/2016 | Hedayat | G01N 15/0656 |
| 9,528,419 B2* | 12/2016 | Aoki | F02D 41/1466 |
| 2015/0168285 A1* | 6/2015 | Hedayat | G01M 15/102 |
| | | | 73/23.33 |
| 2016/0204716 A1* | 7/2016 | Suzuki | B81B 3/0054 |
| | | | 359/230 |

* cited by examiner

METHOD AND SYSTEM FOR RESISTIVE-TYPE PARTICULATE MATTER SENSORS

FIELD

The present description relates generally to the design and use of resistive-type particulate matter (PM) sensors in an exhaust flow that are robust in harsh chemical environments.

BACKGROUND/SUMMARY

Combustion exhaust is a regulated emission and various exhaust aftertreatment devices located in the engine exhaust play a role in detection and controlling of exhaust emissions. Diesel particulate filters (DPF) are commonly used for particulate matter (PM) or soot control, and lean NOx traps (LNT) are used for NOx control. Under lean conditions, an LNT adsorbs oxides of nitrogen (such as nitric oxide NO and nitrogen dioxide $NO_2$, also referred to as NOx for short) produced during engine combustion. Lean-burn engine exhaust contains oxides of sulfur (SOx), derived from fuel and lubricating oil, which compete with NOx for LNT adsorption sites. Unfortunately, SOx is preferentially adsorbed over NOx and forms stable sulfates with the LNT storage materials. As a result, LNT performance gradually declines because fewer storage sites are available for NOx adsorption.

To effectively manage sulfur poisoning of LNT, high temperature desulfation is periodically performed on the LNT. Desulfation requires a high temperature exhaust and cycles of lean and rich conditions to release sulfur from the LNT adsorption sites. However, the hydrogen sulfide ($H_2S$) gas released as a byproduct of desulfation introduces a harsh chemical environment for the various sensors and detectors located downstream of the LNT in the exhaust line. For example, soot sensors located downstream of the LNT, may get degraded in the harsh chemical environment. Typically, resistive-type soot sensors estimate an exhaust soot level based on a correlation between a measured change in electrical conductance (or resistance) between a pair of interdigitated comb electrodes of the sensor with the amount of PM deposited between the measuring electrodes. However, $H_2S$ released as a by-product of desulfation may react electrochemically on the sensor electrodes, thereby corroding the electrodes and reducing the sensitivity of the soot sensors. For example, the reaction of the $H_2S$ with the soot sensor electrode may cause the sensor gain to drift.

Various approaches have been developed for protecting soot sensor electrodes from corrosion resulting from $H_2S$ released as a by-product of LNT desulfation. One example approach is shown by Berger et al. in U.S. Pat. No. 7,543, 477. Therein, the soot sensor electrodes are covered with a protective layer manufactured from an electrically insulating base like aluminum oxide or zirconium dioxide and further doped with a conductive material, such as a metal or graphite. The protective layer may serve to protect the soot sensor electrodes from direct exposure to the harsh chemical environment encountered in the exhaust line.

However, the inventors have recognized potential issues with such an approach. As one example, adding additional protective layer may reduce the electrostatic attraction between the charged soot particles and the soot sensor electrodes and may lead to reduced soot sensor sensitivity. With reduced sensitivity, the soot sensor may not be able to determine the leakage of the particulate filter in a reliable way. Thus errors in the sensor may lead to a false indication of DPF degradation and unwarranted replacement of functioning filters.

The inventors herein have observed that $H_2S$ appears to preferentially react with the negative electrode of the soot sensor. Specifically, following $H_2S$ reaction, the degree of corrosion on the negative electrode was significantly higher than the degree of corrosion on the positive electrode. In view of this observation, the inventors have recognized that corrosion of the soot sensor negative electrode can be reduced by making the negative electrode temporarily appear like the positive electrode. Specifically, during conditions when the level of $H_2S$ in the exhaust is high, such as during desulfation of the LNT, by making the negative electrode have an open circuit floating potential, with no possibility of electron flow through the negative electrode, the selective corrosion of the negative electrode may be reduced.

Thus in one example, corrosion of soot sensor electrodes may be addressed by a method for selectively connecting and disconnecting a positive electrode of interdigitated comb electrodes of a soot sensor to/from a positive voltage and selectively connecting a negative electrode of the interdigitated comb electrodes of the sensor to ground via a measuring resistor. In this way, by varying the coupling of the electrodes of a soot sensor to a positive voltage based on exhaust conditions, $H_2S$-induced corrosion of soot sensor electrodes is reduced.

As one example, the circuitry of a resistive-type particulate matter sensor may be adjusted to include a three-way switch coupled to the negative electrode of the sensor. Based on exhaust conditions, a position of the three-way switch may be adjusted so that the negative electrode is coupled to one of the positive voltage source of the sensor, to ground, or left open. At the same time, a two-way switch may couple or decouple the positive electrode of the sensor to the positive voltage. When the soot sensor is collecting particulate matter in the exhaust, the method includes selectively connecting the positive electrode to the positive voltage (by closing the two-way switch connecting the positive electrode and the positive voltage) and selectively connecting the negative electrode to ground via a measuring resistor (by shifting the three-way switch connecting the negative electrode to the positive and ground to a first position). During desulfation of the LNT, when the exhaust $H_2S$ levels are high, the soot sensor is operated first in a pre-desulfation (prior to desulfation of the LNT) mode and then followed by a desulfation mode. During pre-desulfation of the LNT, the positive electrode may be selectively disconnected from the positive voltage (by opening the two-way switch) and the negative electrode may be selectively connected to the positive voltage (by shifting the three-way switch to a second position). Following this, during desulfation of the LNT, the positive electrode may be maintained disconnected from the positive voltage and additionally the negative electrode may be selectively disconnected from the positive voltage (by shifting a three-way switch to a third or open position).

The technical effect of coupling the negative electrode first to the positive voltage during pre-desulfation, and then disconnecting it during desulfation from both the positive voltage and the ground via a three-way switch of the sensor is that when $H_2S$ is released during desulfation, the negative electrode transiently resembles the positive electrode, and that both the sensor electrodes act as open circuit floating potentials, with reduced possibility of electron flow. During other conditions, such as soot sensor regeneration or LNT regeneration, by adjusting the switch, the negative electrode may be disconnected from both the positive voltage and the ground. This reduces the preferential electrochemical reaction between the released $H_2S$ and the negative electrode. As a result, soot sensor gain drift is reduced, thereby reducing soot sensor corrosion during LNT desulfation. By reducing the gain drift of the soot sensor, sensor accuracy is improved, lowering the risks for false indication of particulate filter degradation. Furthermore reducing gain drift of the soot sensor better enables detection of polluting exhaust for PMs. As such, this reduces the high warranty costs of replacing functional particulate filters and exhaust emissions are improved and exhaust component life is extended.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
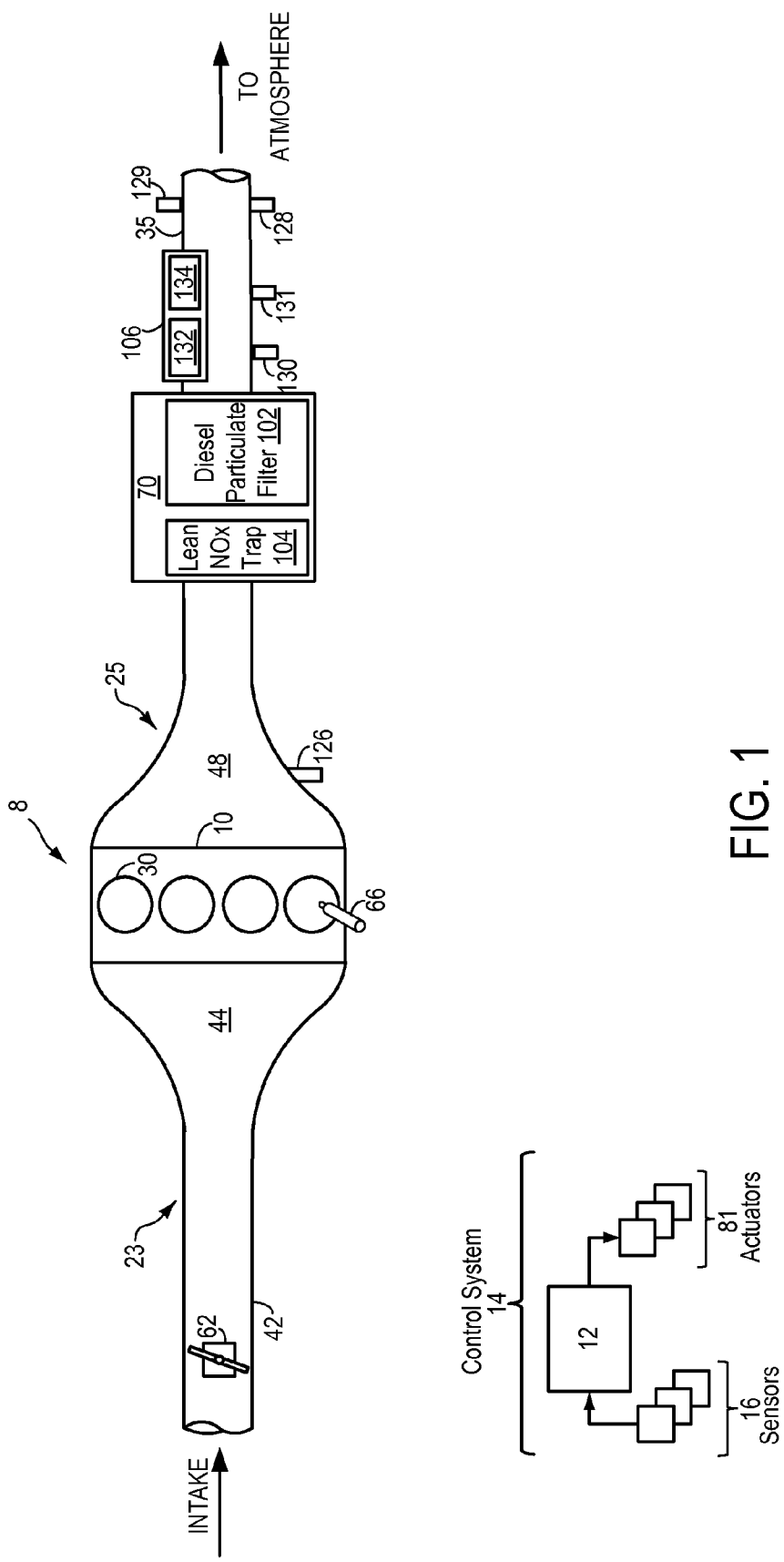
FIG. 1 shows a schematic depiction of an engine fuel system and an associated lean NOx trap (LNT) and a resistive-based exhaust soot sensor, according to the present disclosure.
Figures 2A, 2B:
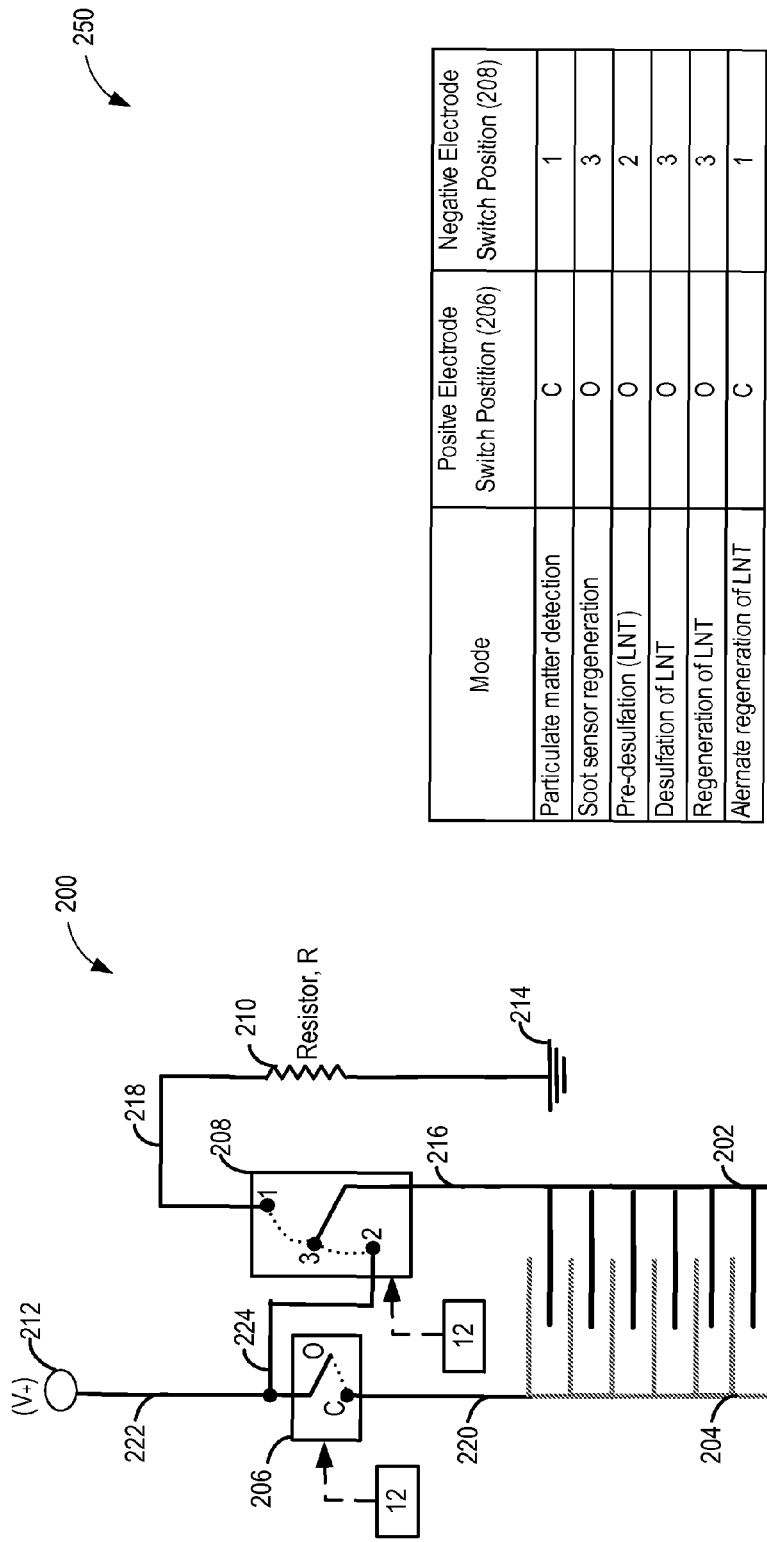
FIG. 2A shows a circuit diagram for the example soot sensor including a plurality of switches.
FIG. 2B shows a table with switch positions corresponding to the different modes of operation of the soot sensor, according to the present disclosure.
Figure 6:
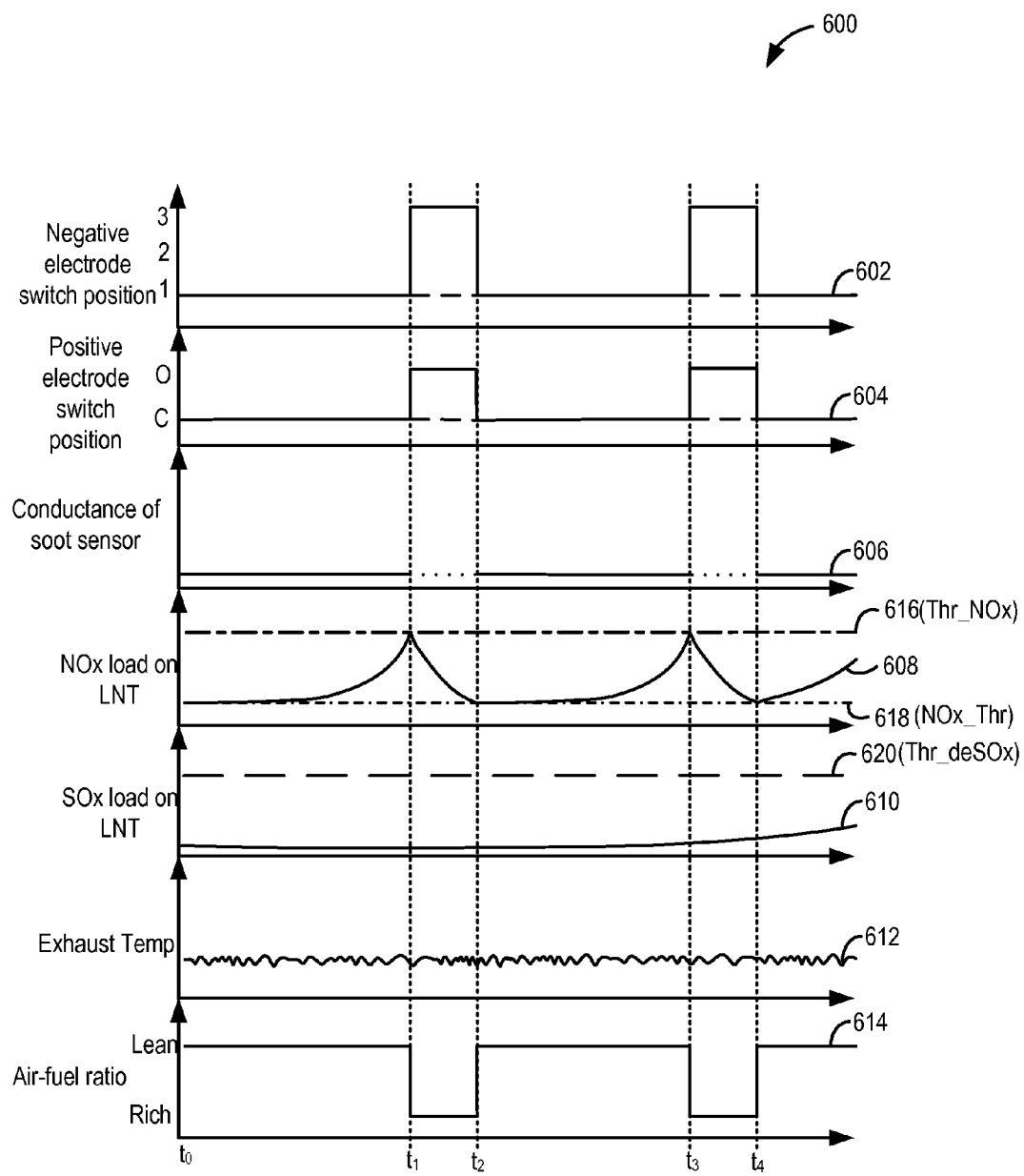
FIG. 6 shows an example relationship between soot sensor circuit switch positions and regeneration of the LNT.
Figure 7:
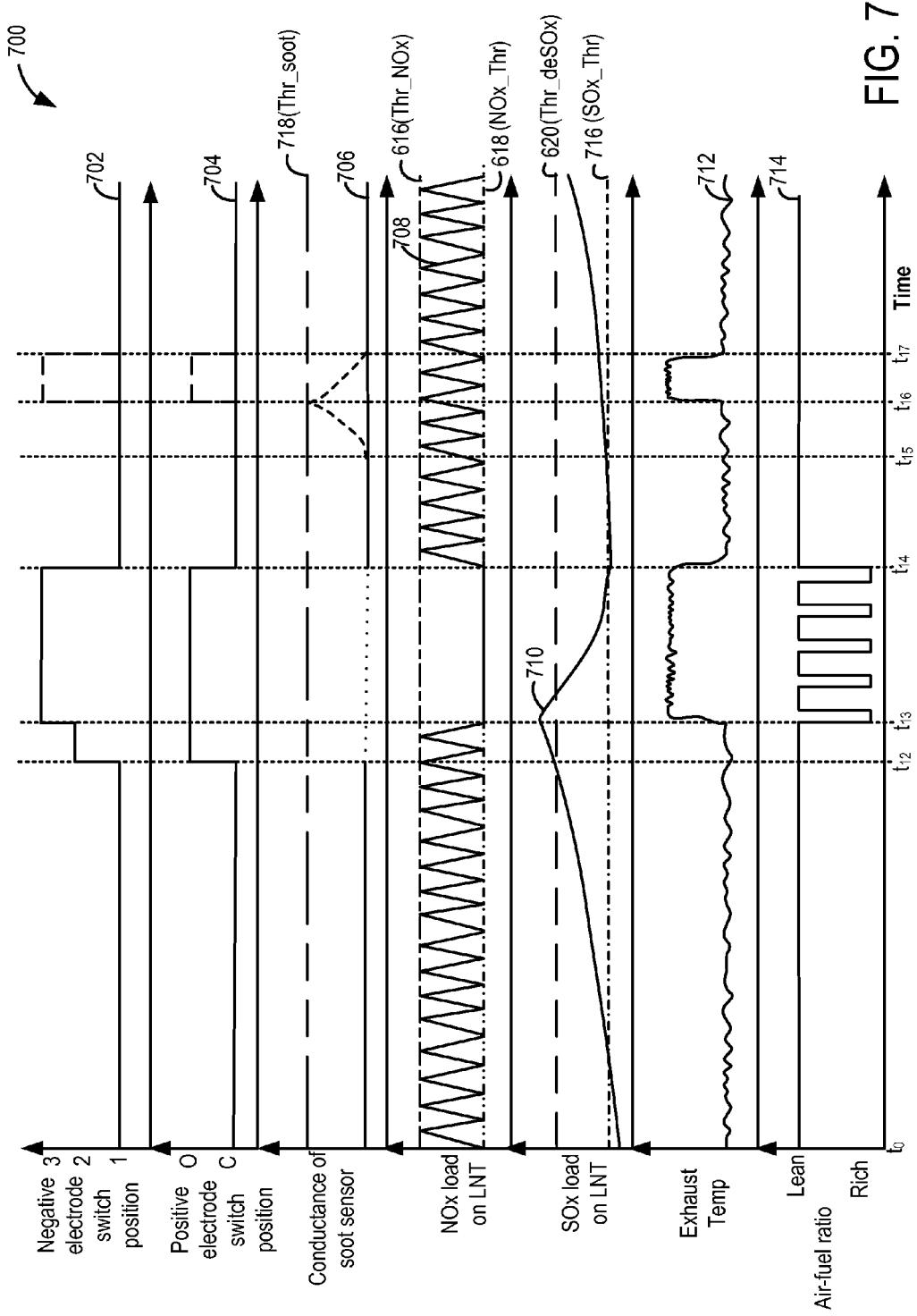
FIG. 7 shows an example relationship between the soot sensor circuit switch positions and desulfation of the LNT.

The following description relates to systems and methods for operating a particulate matter (PM) or soot sensor positioned downstream of a lean NOx trap (LNT) in an engine exhaust line in an engine system, such as in the engine system of FIG. 1. The PM sensor configured with a pair of interdigitated electrodes may be connected to a positive voltage and ground via a plurality of switches as shown in FIG. 2A-B. A controller may be configured to perform a routine, such as the routine of FIG. 3, to change the position of the switches of the soot sensor based on the modes of operation of the LNT and the soot sensor. The controller may also be configured to perform a routine, such as the routine of FIG. 4 to operate the soot sensor in particulate matter detection mode and regenerate the soot sensor based on the soot load on the soot sensor. In addition, the controller may intermittently estimate the exhaust NOx and SOx levels of the LNT, and perform a routine, such as the routine of FIG. 5, to regenerate and desulfate the LNT based on the corresponding NOx and SOx levels on the LNT. An example relationship between soot sensor circuit (position of the switches in the circuit, in particular) and regeneration and desulfation of the LNT are shown in FIGS. 6 and 7. In this way, corrosion of the soot sensor electrodes may be reduced and warranty issues may be avoided.

FIG. 1 shows a schematic depiction of an engine system 8. In one example, engine system 8 is included in a propulsion system, such as an on-road vehicle. The engine system 8 may include an engine 10 having a plurality of cylinders 30. Engine 10 includes an engine intake 23 and an engine exhaust 25. Engine intake 23 may include a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, an after-cooler may be configured to reduce the temperature of intake air compressed by the boosting device (not shown).

Engine exhaust 25 may include one or more emission control devices 70, which may be mounted in a close-coupled position in the exhaust. The emission control devices may include a three-way catalyst, lean NOx conversion device, particulate filter, SCR catalyst, and/or combinations thereof. In one example embodiment, as depicted, emission control device 70 may include a diesel particulate filter (DPF) 102 positioned downstream of a lean NOx trap (LNT) 104. However, in alternate embodiments, the DPF may be positioned upstream of the LNT.

LNT 104 is configured to adsorb exhaust NOx species generated under lean combustion conditions, and further configured to reduce and release the adsorbed NOx under rich conditions, wherein lean and rich refer to the combustion air-fuel ratio (AFR) relative to stoichiometry. For gasoline engines, the stoichiometric AFR is typical about 14.7:1, which implies 14.7 parts of air to one part of fuel. A lower AFR (that is, less than 14.7) indicates less air and more fuel and reflects a rich mixture. Similarly, a higher AFR (greater than 14.7) indicates more air and less fuel and reflects a lean mixture. LNT 104 generally includes a NOx adsorbent and a catalyst. The adsorbent is typically an alkali or alkaline earth compound, and the catalyst is typically a combination of precious metals including Pt and Rh; alkaline, alkaline earth, or rare earth metals, e.g., K, Ba or Ce. With Barium Nitrate absorbent as an example, under lean oxide conditions, the catalyst speeds oxidizing reactions that lead to NOx adsorption. However under rich conditions, Barium Nitrate decomposes to Barium Oxide and $NO_2$, and then in further reactions $NO_2$ can further reduce to NO and then further reduce to $N_2$. The reductant gases are typically $H_2$, CO, and various hydrocarbons. The typical temperature of the LNT for these absorptions and reactions is 200° C. to 400° C. A typical cycle would be approximately 60 seconds of absorption of NOx while lean (e.g., typically 20:1 AFR to 30:1 AFR) followed by 5 seconds of denitration while rich (e.g., 12:1 AFR to 14:1 AFR). During lean absorption, NOx reacts with barium oxide to form barium nitrate. A NOx sensor 130 may be positioned downstream of the LNT 104 to determine the exhaust NOx load on the LNT. Regeneration or denitration or deNOx, as this reducing process is called, is performed from time-to-time to remove accumulated NOx.

In addition to accumulating exhaust NOx, LNT 104 accumulates oxides of sulfur (SOx), derived from fuel and lubricating oil, which compete with NOx for LNT adsorption sites. SOx is preferentially adsorbed over NOx and forms semi-stable sulfates with the LNT storage materials. As a result, LNT performance gradually declines because fewer storage sites are available for NOx adsorption. Desulfation (or DeSOx) is the process by which the SOx is removed from the LNT, and so refresh the LNT to allow NOx absorption. Desulfation of LNT is carried out much less frequently than regeneration of LNT. Desulfation (also called "deSOx") requires a high temperature exhaust and cycles of lean and rich conditions to release sulfur from the LNT adsorption sites. In one example, LNT may be subjected to five cycles of 10 s rich and 18 s lean mixture at temperatures in excess of 700° C. during desulfation. This wobbling or cycling can vary from system to system, but the goal is to remove the adsorbed sulfur from the LNT, while maximizing the $SO_2$ gas emitted downstream and minimizing the H2S gas emitted downstream of the LNT. The $SO_2$ is less corrosive to the sensor electrodes and is not a poisonous gas at low concentrations (which $H_2S$ is). The hydrogen sulfide ($H_2S$) gas released as a byproduct of desulfation not only is a poisonous gas and has an obnoxious smell, but it also introduces a harsh chemical environment for the various sensors and detectors located downstream of the LNT in the exhaust line.

The diesel particulate filter (DPF) 102 located downstream of LNT 104, temporarily filters PMs from entering gases. DPF 102 may have a monolith structure made of, for example, cordierite or silicon carbide, with a plurality of channels inside for filtering particulate matter from diesel exhaust gas. Tailpipe exhaust gas that has been filtered of soot, following passage through DPF 102, may be measured in the soot sensor 106 (also called PM sensor) and expelled to the atmosphere via exhaust passage 35. In the depicted example, soot sensor 106 is a resistive sensor that estimates a soot leakage of the DPF 102 based on a change in conductance measured across the electrodes of the soot sensor 106. If the soot emission from the DPF 102 as determined from the output of the soot sensor 106 is greater than the threshold soot emission, then the DPF 102 may be determined to be leaking and damaged, and in need of replacement. As such, when the conductance of the soot sensor reaches a threshold, the soot sensor may also be regenerated by heating the soot sensor until the soot particles are burned off. The response time for the accumulation of soot emission and thus the response time to achieve a threshold of conductance is a measure of DPF leakage.

Soot sensor 106 may further include a pair of planar interdigitated electrodes on the surface of the soot sensor. Any degradation of these electrodes may change the conductance measured and also may affect the rate of soot collected. Thus, the response time may become faster or slower for a given DPF soot leakage rate. This may lead to type 1 and type 2 errors for DPF leakage detection. The soot sensor may include a sensor control unit (SCU) 134 and plurality of switches 132. A schematic view 200 of the soot sensor 106 and the soot detection circuit is shown with reference at FIG. 2. Electrodes of soot sensor 106 may get corroded due to $H_2S$ released during desulfation of LNT 104, for example. As elaborated herein with reference to FIG. 2, by operating the soot detection circuitry in accordance with the modes of operation of the soot sensor and the LNT, it may be possible to minimize corrosion of the electrodes.

Turning now to FIG. 2, a schematic view 200 of an example embodiment of a particulate matter (PM) sensor (such as soot sensor 106 of FIG. 1) and a PM detection circuit is shown. The PM sensor 106 includes a pair of planar interdigitated electrodes 202 and 204 forming a "comb" structure. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes 202 and 204 are formed on a substrate (not shown) of the soot sensor that is typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes. The spacing between the comb "tines" of the two electrodes may typically be in the range from 10 micrometers to 100 micrometers with the linewidth of each individual "tine" being about the same value, although the latter is not necessary. Since the electrodes are subjected to the direct exhaust gas flow, corrosion and contamination of the sensor surface may disadvantageously occur which may have an interfering effect on the measurement. In some examples, the sensor surfaces may include a protective layer manufactured from an electrically insulating base material such as aluminum oxide or zirconium dioxide for example, and doped with conductive material such as a metal or graphite. However, it may be possible to minimize degradation of the sensor electrodes by modifying the soot detection circuitry which may then be used for sensors with or without the protective layer covering the electrodes.

A positive electrode 204 of the pair of interdigitated electrodes may be connected with connecting wires 220 and 222 to a positive voltage 212 via a switch 206. A controller (such as controller 12 of FIG. 1) may control the switch 206 to selectively connect and disconnect the positive electrode 204 of the interdigitated comb electrodes of soot sensor 106 to and from a positive voltage 212. Alternately, the controller 12 may control a sensor control unit 134 of the soot sensor 106 that further controls the operation of the switch 206. Herein, the positive electrode 204 is electrically coupled to the positive voltage 212 via a two-way switch and selectively connecting the positive electrode to the positive voltage includes closing the two-way switch or moving the switch to a first closed (C) position. The positive electrode 204 may be selectively disconnected from the positive voltage 212 by opening the two-way switch 206. Opening the switch 206 includes, moving the switch to a second open (O) position thereby decoupling the positive electrode 204 from the positive voltage 212.

A negative electrode 202 of the pair of interdigitated electrodes may be connected to a switch 208 via a connecting wire 216. The switch 208 is a three-way switch and may be further controlled by controller 12 of FIG. 1, for example. Alternately, the switch 208 may be controlled by the sensor control unit 134 which is in turn controlled by the controller 12. The three-way switch 208 includes three positions labelled as 1, 2 and 3 in view 200. The three way switch 208 is located between the negative electrode and the measuring resistor 210. The negative electrode 202 of the interdigitated comb electrode of the soot sensor 106 may be selectively connected to ground 214 via a measuring resistor 210 when the switch 208 is in the first position (position 1). The negative electrode 202 of the interdigitated comb electrode of the soot sensor 106 may be selectively connected to the positive voltage 212 by shifting the three-way switch 208 to a second position (position 2). When the switch 208 is in position 2, the negative electrode is connected to the positive voltage 212 by connecting wires or circuit traces 216, 224 and 222. The negative electrode 202 may be selectively disconnected from both the positive voltage 212 and ground 214 by shifting the three-way switch 208 to a third position (position 3). When the switch 208 is in position 3, the negative electrode 202 is decoupled from both the positive voltage 212 and the ground 214, and is left open. Thus the three-way switch 208 may include two closed positions (position 1 and 2), and one open position (position 3). However, in the closed positions, the negative electrode 202 is either connected to the positive voltage 212 (position 2) or the ground 214 (position 1). The switches 206 and 208 may be part of a plurality of switches 132 in the SCU 106 of FIG. 1 or the switches 206 and 208 may be located elsewhere. The design and implementation of the circuit may be further simplified by including a three-way switch in both locations, that is, both 206 and 208 may be three-way switches. While the three-way switch connected to the negative electrode may be operated as described above, the three-way switch connected to the positive electrode may include two open positions and one closed position to operate it as described above.

By shifting the switches 206 and 208 to appropriate positions, the soot sensor may be operated in several modes. When the soot sensor 106 is collecting particulates in the exhaust, the soot sensor is operated in particulate matter detection mode. In the particulate matter detection mode, the positive electrode 204 is selectively connected to the positive voltage 212 by closing the switch 206 and the negative electrode is selectively connected to ground 214 via the measuring resistor 210 by moving the switch 208 to the first closed position (position 1) as shown in table 250 of FIG. 2B. In this configuration, there is a potential gradient between the positive electrode 204 and the negative electrode 202 since the positive electrode is connected to $V_+$ and the negative electrode is connected to ground (0V). The value of $V_+$ may be any value higher or lower than ground to allow creating an electric field. Typically, a direct current voltage higher than battery voltage is used. The engine generated soot particles are typically charged, and these particles undergo electrostatic attraction in the potential gradient between the positive and negative electrode, and as a result the soot particles stack up to form a dendritic whisker between the positive and negative electrodes. When the dendritic whisker grows long enough, it bridges the gap between the electrodes, thereby forming a soot bridge and establishing connectivity between the tines of the electrodes. As a result, the resistance between the electrode pair changes and this change in resistance is used as a measure of the soot particles or soot accumulated onto the tines of the sensor electrodes 202 and 204 (called sensor soot load) in the exhaust. The soot sensor 106 may be positioned downstream of the LNT 104 and the DPF 102, as shown in FIG. 1. The output of the soot sensor may be used to determine the leakage of soot past the DPF 102 and so diagnose the functioning of the DPF.

During conditions when the exhaust soot load of the soot sensor is higher than a threshold sensor soot load, the soot sensor may be regenerated by heating the sensor substrate via a heating element (not shown) to burn the accumulated soot particles from the surface of soot sensor 106. By intermittently regenerating the surface of soot sensor 106, it may be returned to a condition more suitable for collecting exhaust soot. In addition, accurate information pertaining to the exhaust soot level may be inferred from the sensor regeneration and relayed to the controller. When the soot sensor is regenerated, the positive electrode may be selectively disconnected from the positive voltage by opening the switch 206 (shown in table 250 of FIG. 2B). In addition, the negative electrode may be selectively disconnected from ground by shifting the switch 208 to a third or open position (position 3, shown in table 250 of FIG. 2B).

When the exhaust NOx and SOx load of the LNT is above a NOx and SOx load of the LNT, respectively, the LNT may be regenerated and desulfated to reduce the corresponding NOx and SOx load. As described with reference to FIG. 1, during regeneration and desulfation of the LNT harmful chemicals may be released in the exhaust line. In order to reduce electrochemical damage to the soot sensor electrodes in such a reactive environment, the positive and the negative electrodes of the soot sensor may be disconnected from the positive voltage (by opening switch 206) and ground (by shifting switch 208 to the third position). Thus, while operating the LNT in a regeneration mode, the positive electrode 206 of the soot sensor may be selectively disconnected from the positive voltage 212 and the negative electrode 202 may be selectively disconnected from each of the positive voltage and the ground by shifting the three-way switch 208 to the third position (table 250 of FIG. 2). Alternatively, while the LNT is regenerated, the soot sensor may be operated in particulate matter detection mode and may continue to detect soot in the exhaust. As described earlier, in the particulate matter detection mode, the positive electrode 206 of the soot sensor is connected to the positive voltage 212 and the negative electrode 202 is connected to ground by shifting the three-way switch 208 to the first position (table 250 of FIG. 2).

During desulfation of the LNT, $H_2S$ gas is released and the negative electrode may undergo additional degradation due to the reactive nature of electrochemical reaction occurring between $H_2S$ and the negative electrode surface. $H_2S$ may preferentially react with the negative electrode and form a salt (PtS, for example) as a surface corrosion product on the negative electrode, for example. The inventors have recognized that it may be possible to reduce degradation of the negative electrode by selectively connecting the negative electrode to the positive voltage prior to desulfation of the LNT, so that the negative electrode may transiently resemble the positive electrode. As an example, prior to SOx load of LNT reaching a threshold, that is during a mode called pre-desulfation (table 250 of FIG. 2), the positive electrode may be selectively disconnected from the positive voltage by opening the two-way switch 206 and the negative electrode may be selectively connected to the positive electrode 212 by shifting the three-way switch 208 to a second closed position. In this configuration, connecting wire 216 couples the negative electrode to switch 208, which when closed in second position, connects the negative electrode via connecting wires 224 and 222 to the positive voltage 212. The two-way switch 206 and the three-way switch 208 may be in closed positions as described above for a threshold time (4 s, for example) prior to the start of desulfation. However, when the desulfation mode begins, the positive electrode may be maintained open, and the negative electrode may be disconnected from both the positive voltage and the ground by shifting the three-way switch to third (open) position, as described earlier. The different modes of operation of the soot sensor and the LNT and the corresponding positions of the switches 206 and 208 are shown in table 250 of FIG. 2B.

The control system 14 of FIG. 1 is shown receiving information from a plurality of sensors 16 (various examples of which are described herein) and sending control signals to a plurality of actuators 81 (various examples of which are described herein). As one example, sensors 16 may include exhaust gas sensor 126 (located in exhaust manifold 48), temperature sensor 128, pressure sensor 129 (located upstream and/or downstream of emission control device 70), soot sensor 106, NOx sensor 130, SOx sensor 131, etc. Other sensors such as additional pressure, temperature, air/fuel ratio, and composition sensors may be coupled to various locations in the vehicle system 6. As another example, the actuators may include fuel injectors 66, throttle 62, DPF and LNT valves that control filter and trap regeneration (not shown), two-way and three-way switches in PM detection circuitry, sensor control unit etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. Example routines are described herein with reference to FIGS. 3-6.

Figure 3:
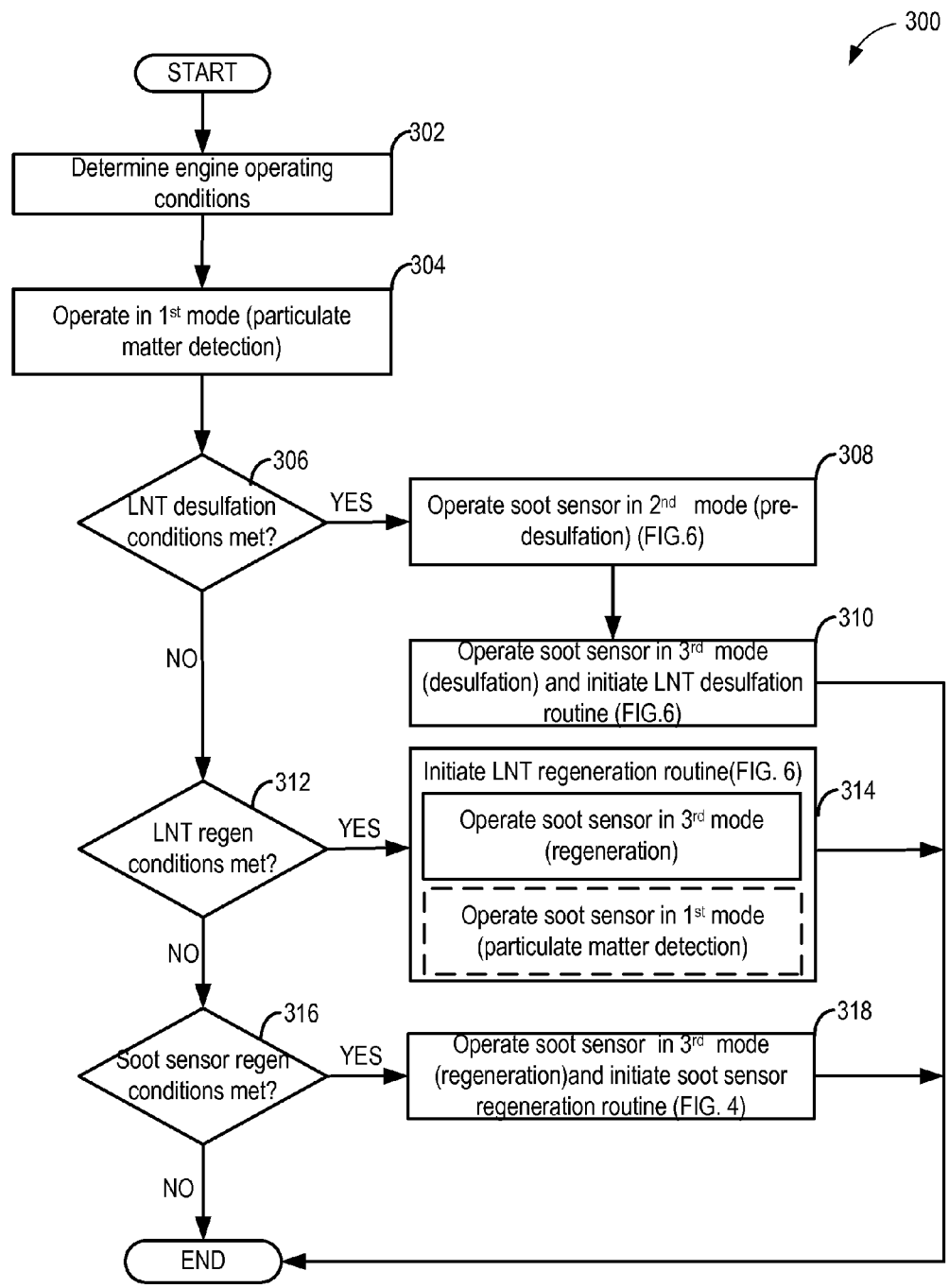
FIG. 3 shows a high level flow chart for operating the soot sensor in one of a plurality of modes, according to the present disclosure.

FIG. 3 shows a method 300 for operating the soot sensor in one of three modes. Instructions for carrying out method 300 and the rest of the methods included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 302, method 300 includes determining engine operating conditions. Engine operating conditions determined may include, for example, engine speed, engine temperature, various exhaust air-fuel ratios, various exhaust temperatures, soot load on soot sensor, soot load on DPF, NOx and SOx load on an exhaust LNT, ambient temperature, duration (or distance) elapsed since a last regeneration and desulfation of the LNT, etc. At 304, in response to the soot load on the soot sensor being lower than the threshold as measured by the measuring resistor (such as resistor 210 shown in FIG. 2A for example), the soot sensor may be operated in a first mode, specifically a particulate matter detection mode, wherein the positive electrode of the soot sensor is electrically coupled to the positive voltage by actuating a first switch (coupled to the positive electrode) to a closed position. In addition, the negative electrode of the soot sensor is electrically coupled to ground via a measuring resistor by actuating a second switch (coupled to the negative electrode) to a first, closed position. While the soot sensor is continuing to collect particulates in the exhaust, the LNT may be accumulating exhaust NOx and SOx as described earlier.

At 306, method 300 may determine if LNT desulfation conditions are met. As explained earlier, sulfur poisoning of the LNTs due to accumulation of SOx on the LNT which may degrade the operation of the LNT. The rate and degree of sulfur poisoning may depend on the fuel sulfur concentrations and mileage accumulated, for example. To maintain the NOx trapping efficiency, the LNT may be intermittently desulfated. Desulfation conditions are considered met if exhaust SOx load on the LNT is greater than a threshold. The threshold may be based on the NOx load of LNT. As explained earlier, SOx is preferentially adsorbed over NOx and forms stable sulfates with the LNT storage materials. As a result of SOx adsorption, LNT performance gradually declines because fewer storage sites are available for NOx adsorption. The threshold of desulfation may be determined as the threshold when NOx adsorption efficiency of the LNT begins to decline. Alternately, the SOx load may be predetermined based on the age of the LNT and SOx adsorption efficiency of the LNT, for example. During desulfation of the LNT, the exhaust $H_2S$ levels are high and the soot sensor may get corroded in the harsh environment. Thus, if desulfation conditions are met at 306, prior to initiating desulfation, method 300 proceeds to 308, where the soot sensor may be operated in a second mode or pre-desulfation mode and method proceeds to 310 where the soot sensor may be operated in a third mode or desulfation mode and the LNT desulfation routine as described in FIG. 6 may be initiated and the method ends. However, if LNT desulfation conditions are not met at 306, method 300 may proceed to 312, where it may be determined if the LNT regeneration conditions are met. Due to the finite capacity of NOx adsorption sites on the LNT, when the exhaust NOx load on the LNT reaches a threshold, the LNT may need to undergo a rich regeneration. Under the LNT regeneration conditions, the absorbent (metal nitrate) decomposes and is reduced to $N_2$ over the catalyst as previously described. If LNT regeneration conditions are met or the NOx load of the LNT is greater than a threshold NOx load, method 300 proceeds to 314, where LNT regeneration routine described in FIG. 6 may be initiated. While LNT is regenerated, the soot sensor may either be operated in a regeneration mode or in the particulate matter detection mode. Regenerating the LNT includes creating rich-burn conditions where the absorbent decomposes and is subsequently reduced to $N_2$ over the LNT catalyst and the DPF. The LNT regeneration may be performed more frequently than LNT desulfation, for example.

However if LNT regeneration conditions are not met when checked at 312, method 300 proceeds to 316, where soot sensor regeneration conditions may be determined. While operating the soot sensor in the first mode, the soot sensor may continue to collect exhaust. The soot load may be continually inferred and updated based on resistance or conductance changes that occur between the electrodes of the sensor as a result of soot deposition. At 316, it may be determined if soot sensor regeneration conditions are met. In one example, when the soot load on the soot sensor reaches or exceeds a threshold as measured by conductance across the sensor electrodes (such as electrodes 202 and 204 shown in FIG. 2A for example), or when the electrical current through the measuring resistor (such as resistor 210 of FIG. 2A, for example) exceeds a threshold, soot sensor regeneration conditions may be confirmed. If soot sensor regeneration conditions are met, such as when the soot load of the soot sensor is greater than a threshold soot load, method 300 proceeds to 318 where the soot sensor may be operated in a third mode, specifically a regeneration mode. Further, a soot sensor regeneration routine as described in FIG. 4 may be initiated at 318 and method 300 ends. Regenerating the soot sensor during the regeneration mode may include heating up the sensor using heating elements (such as a heating element coupled to the sensor, not shown) until the sensor electrodes are burned free of the soot deposited on them. In general, the soot sensor is regenerated less frequently than LNT, for example, to remove the exhaust soot collected on the soot sensor electrodes. In some cases, for a non-leaking DPF for example, the soot sensor may rarely be regenerated over a drive cycle. Thus, for these conditions, method 300 ends and then starts again going back to 302.

In this way, a soot sensor may be operated in one of a plurality (herein three) modes based on exhaust conditions. A controller may be configured to transition the sensor between the different modes by adjusting the position of a first switch coupled to a positive electrode of the soot sensor and a second switch coupled to a negative electrode of the soot sensor. The various switch positions and the operating of the soot sensor in the plurality of modes is now elaborated with reference to FIGS. 4-6.

Figure 4:
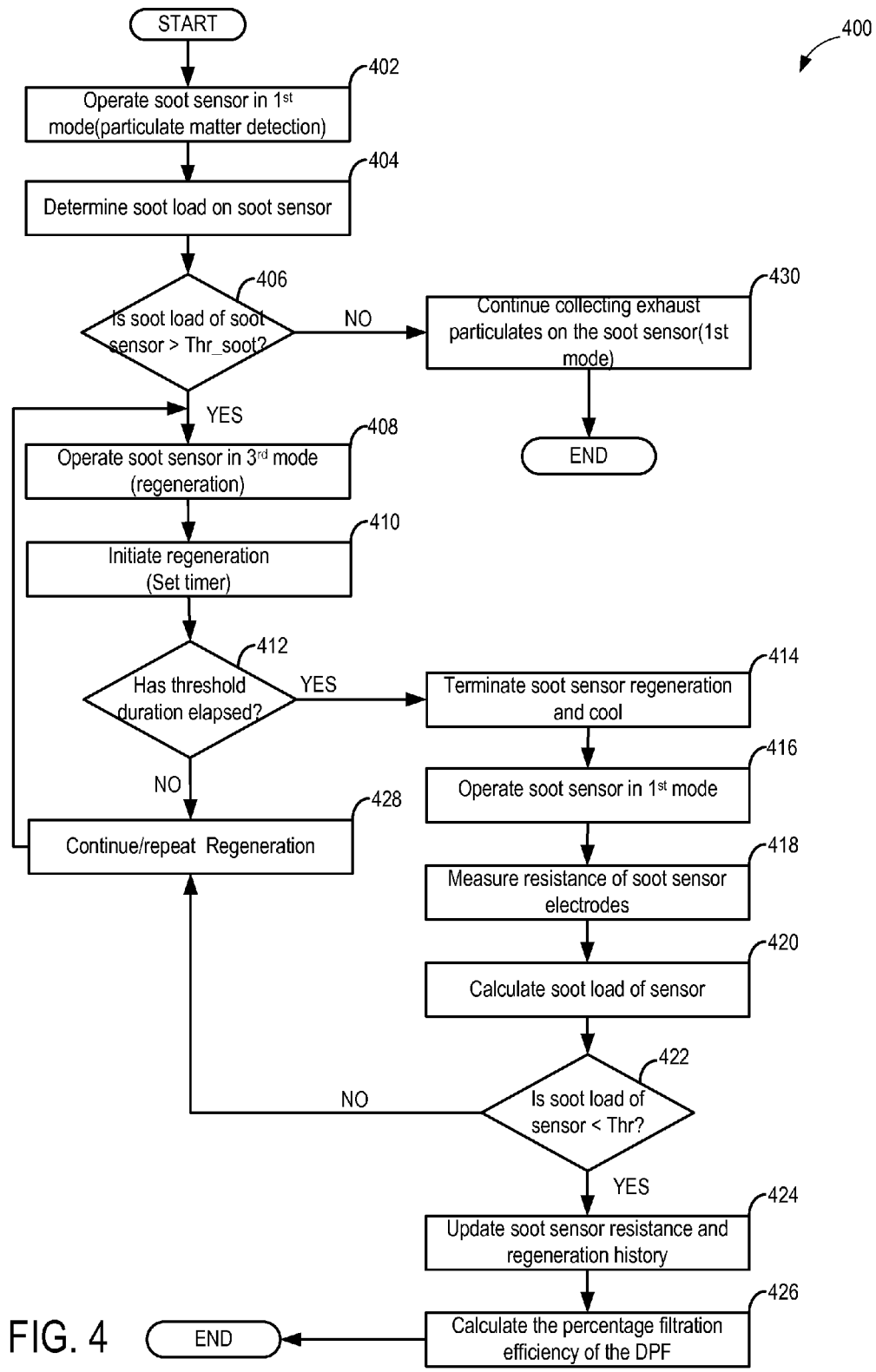
FIG. 4 shows a high level flow chart depicting a method for performing regeneration of the soot sensor, according to the present disclosure.

Turning now to FIG. 4, a method 400 for regenerating the soot sensor (such as a soot sensor 106 shown at FIG. 1, for example) is shown. At 402 the soot sensor may be operated in the first mode (particulate matter detection mode). Operating the soot sensor in the particulate matter detection mode includes closing a first two-way switch and shifting a second three-way switch to a first position. However, if the soot sensor is already in particulate detection mode, then at 402, the soot sensor may be maintained in the particulate matter detection mode by maintaining the two-way switch closed and further maintaining the three-way switch in the first closed position. At 404, the soot load on the soot sensor may be determined. The soot load of the soot sensor may be determined based on a resistance measured across the soot sensor electrodes for example. At 406, it may be determined if the soot load on the soot sensor is greater than a threshold load of soot, Thr_soot. As the soot load on the sensor increases, the resistance decreases. When the soot load on the sensor is greater than the threshold, or when a resistance of the sensor adjusted for temperature drops to a threshold resistance, the soot sensor may need to be regenerated to enable further soot detection. If the soot sensor load is higher than the threshold, then method 400 proceeds to 408, where the soot sensor may be transitioned from the particulate matter detection mode to a third (soot sensor regeneration) mode. Operating the soot sensor in the regeneration mode includes performing a series of operations from 408 through 426. Operating the soot sensor in regeneration mode includes at 408, opening the first, two-way switch of the sensor to selectively disconnect the positive electrode of the soot sensor from the positive voltage (of a voltage source and shifting the second, three-way switch of the sensor to a third position to selectively disconnect the negative electrode from both the positive voltage and the ground. It will be appreciated that the opening of the first, two-way switch coupled to the positive electrode and the shifting of the second, three-way switch coupled to the positive electrode to the third position may be performed concurrently. In alternate examples, however, they may be performed sequentially. In further examples, they may be performed in reverse sequence where the three-way switch may be shifted to the third position, followed by opening the two-way switch.

Upon adjusting the position of the switches, regeneration of the soot sensor may be initiated at 410 and the soot sensor may be regenerated by heating up the sensor. The soot sensor may be heated by actuating a heating element coupled thermally to the sensor electrode surface, such as a heating element embedded in the sensor, until the soot load of the sensor has been sufficiently reduced by oxidation of the carbon particles between the electrodes. The soot sensor regeneration is typically controlled by using timers and the timer may be set for a threshold duration at 410. Alternatively, the sensor regeneration may be controlled using a temperature measurement of the sensor tip, or by the control of power to the heater, or any or all of these. When timer is used for soot sensor regeneration, then method 400 includes checking if the threshold duration has elapsed at 412. If the threshold duration has not elapsed, then method 400 proceeds to 428 where the soot sensor regeneration may be continued. If threshold duration has elapsed, then method 400 proceeds to 414 where the soot sensor regeneration may be terminated. Further, the sensor electrodes may be cooled to the exhaust temperature for example. Method 400 proceeds to 416 where the soot sensor may be transitioned from regeneration mode to particulate matter detection mode by closing the two-way switch and shifting the three-way switch from the third position to the first position. Method 400 proceeds to 418 where the resistance between the electrodes of the soot sensor is measured. From the measured resistance, possibly compensated for temperature, the soot load of the soot sensor (i.e., the accumulated soot between the electrodes of the soot sensor) may be calculated at 420 and the method proceeds to 422. At 422, the calculated soot load of the soot sensor may be compared with a threshold, Thr. The threshold Thr, may be a lower threshold, lower than Thr_soot, indicating that the electrodes are sufficiently clean of soot particles. In one example, the threshold may be a threshold below which regeneration may be terminated. If the soot load continues to be greater than Thr, indicating that further regeneration may be required, method 400 proceeds to 428 where soot sensor regeneration may be repeated. However, if the soot sensor continues to undergo repeated regenerations, the controller may set error codes to indicate that the soot sensor may be degraded or the heating element in the soot sensor may be degraded. If the soot load is lower than the threshold Thr, indicating that the electrode surface is clean, method 400 proceeds to 424, where the soot sensor resistance and regeneration history may be updated and stored in memory. For example, a frequency of soot sensor regeneration and/or an average duration between sensor regenerations may be updated. At 426, various models may then be used by the controller to calculate the percentage efficiency of the DPF the filtration of soot. In this way, the soot sensor may perform on-board diagnosis of the DPF.

The engine exhaust passage may include one or more soot sensors positioned upstream and/or downstream of the DPF for determining a soot load of the DPF. When the soot sensor is positioned upstream of the DPF, based on the resistance change following soot deposited on the electrodes, a soot load on the sensor may be inferred. The soot load thus determined, may be used to update the soot load on the DPF, for example. If the soot load on the DPF is greater than a threshold for DPF regeneration, then the controller may adjust engine operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF. Additionally, during the filter regeneration, the soot sensor may be operated in a regeneration mode, as described in FIG. 4. By selectively disconnecting both the positive electrode of the soot sensor (from the positive voltage) and the negative electrode of the soot sensor (from both the positive voltage and ground) during the regeneration of the exhaust particulate filter, the electrodes may be open hence resilient to electrochemical damage.

Upon terminating the DPF regeneration, the soot sensor may be transitioned to the particulate matter detection mode by closing the first switch to connect the positive electrode to the positive voltage, and shifting the second to the first position to connect the negative electrode to the ground through the measuring resistor, for example. Alternately, if the soot sensor regeneration conditions are met, then the soot sensor may be operated in regeneration mode, by maintaining the positive electrode and negative electrode open, by opening the first switch and shifting the second switch to position 3 as described in FIG. 4. However, if the LNT regeneration or desulfation conditions are met, then the soot sensor may be operated in one of regeneration or pre-desulfation or desulfation modes as elaborated in FIG. 5.

Figure 5:
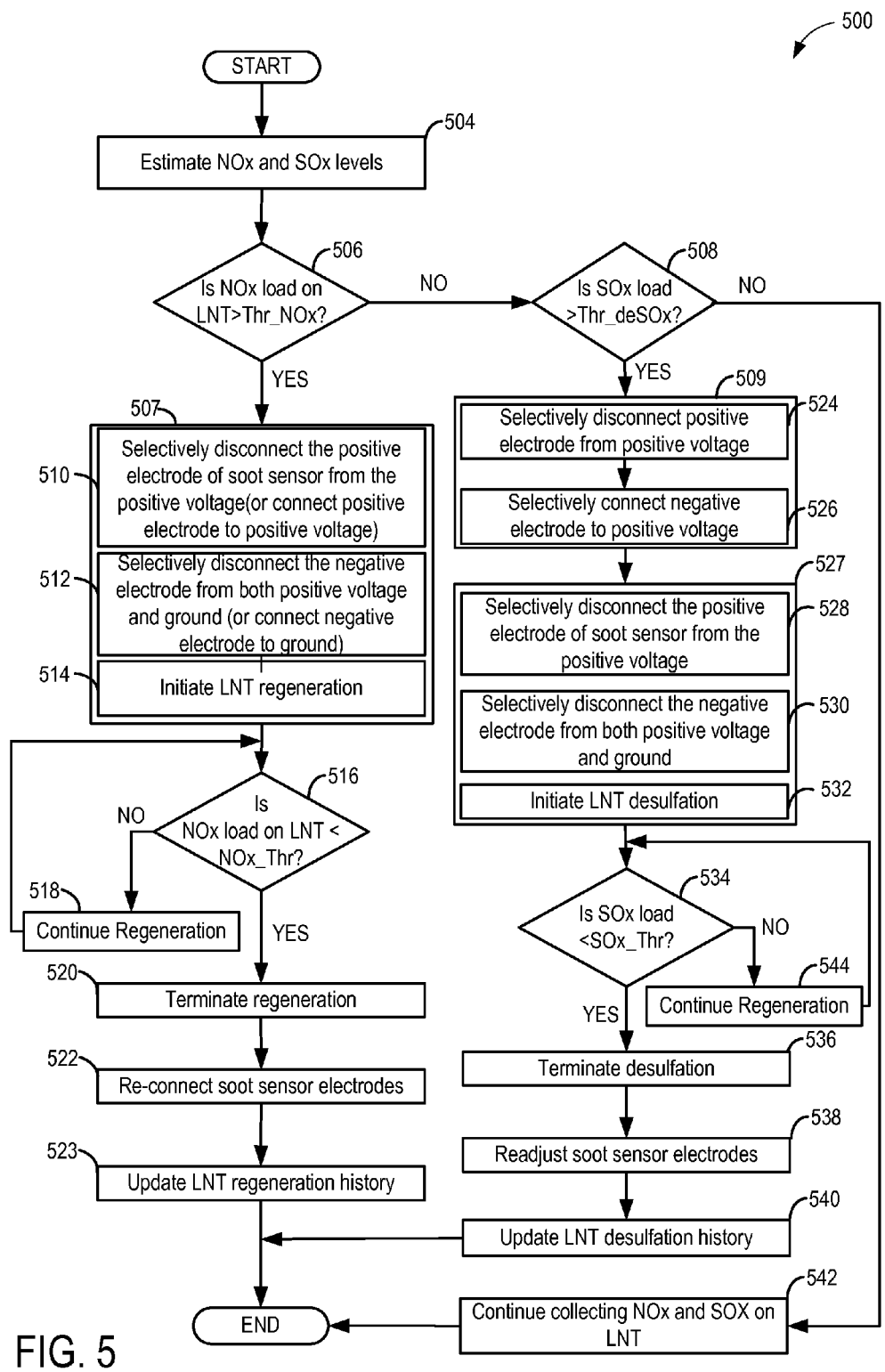
FIG. 5 shows a high level flow chart for regenerating and desulfating the LNT, according to the present disclosure.

Turning now to FIG. 5, a method 500 for regenerating and desulfating an exhaust LNT, while adjusting operation of an exhaust soot sensor is shown. At 504 the exhaust NOx and SOx levels on the LNT may be estimated. As such, the LNT may be configured to trap NOx from the exhaust flow when the exhaust flow is lean (that is, leaner than stoichiometry, with more oxygen from air than there is reducing fuel gas to combust it all) and to reduce the trapped NOx when the exhaust flow is rich (that is, richer than stoichiometry, with more fuel reductant than oxidizing gases). At 506, it may be determined if the NOx load on the LNT is greater than a threshold, Thr_NOx. As mentioned earlier, due to a finite capacity of NOx adsorption sites on the LNT, when the exhaust NOx load on the LNT reaches a threshold, the LNT may undergo a rich regeneration. Under such conditions, absorbent nitrate decomposes to NO and $O_2$ and NO is subsequently reduced to $N_2$ over the catalyst. The threshold may be determined as the maximum load on the LNT at which the LNT regeneration is initiated. If the exhaust NOx load on LNT is greater than the threshold when checked at 506, method 500 proceeds to 507 where the LNT may be regenerated. However, while regenerating the LNT, the soot sensor may be either be operated in regeneration or particulate matter detection mode. For example, at 510, when operated in regeneration mode, the positive electrode of the soot sensor may be selectively disconnected from the positive voltage and at 512, the negative electrode of the soot sensor may be selectively disconnected from both the ground and the positive electrode. In this way, the reducing gases emitted during the regeneration of the LNT do not affect the electrodes of the soot sensor. Alternatively, it may be determined for some calibrations and applications that the soot sensor be operated in particulate detection mode during LNT regeneration. During these condition, the positive electrode of the soot sensor may be selectively connected (or maintained connected) to the positive voltage and the negative electrode of the soot sensor may be selectively connected (or maintained connected) to ground. In this way, the soot sensor may be operated either in regeneration or particulate matter detection mode during regeneration of LNT as described earlier. At 514, LNT regeneration may be initiated to remove the accumulated exhaust NOx. The engine controller may have stored instructions to send a regeneration signal to the regeneration circuit responsive to the NOx load on the LNT. Regeneration of the LNT typically involves the fuel injection rate to make the exhaust rich. The typical temperature of the LNT for these absorptions and reactions is 200° C. to 400° C. A typical cycle would be approximately 60 seconds of absorption of NOx while lean (e.g., typically 20:1 AFR to 30:1 AFR) followed by 5 seconds of regeneration while rich (e.g., 12:1 AFR to 14:1 AFR). Thus, during regeneration of the LNT the soot sensor may be operated either in the third (regeneration) mode or in the first (particulate matter detection) mode. During regeneration of the LNT, operating the soot sensor in regeneration mode includes disconnecting the positive electrode from the positive voltage by opening the first switch to electrically decouple the positive electrode from the positive voltage. Further in soot sensor regeneration mode, disconnecting the negative electrode from both the ground and the positive electrode involves shifting the second switch to an open (third position) to electrically decouple the negative electrode from each of the positive voltage and the ground. The technical effect of opening both the switches, is that the soot sensor electrodes are disconnected from positive voltage and ground, thereby reducing the chances of any chemical reaction occurring on the surface of the electrodes due to the released NOx as a result of regeneration of the LNT. Alternatively, the soot sensor may be continue to collect particulates between its electrodes during LNT regeneration. If operated in particulate matter detection mode, the positive electrode of the soot sensor may be connected to the positive voltage by closing the first switch to electrically couple the positive electrode to the positive voltage. In addition, the negative electrode of the soot sensor may be connected to ground by shifting the second switch to the first position to electrically couple the negative electrode to the ground via the measuring resistor. However, during LNT regeneration if the soot sensor if already in the particulate matter detection mode, then it may be maintained in the same mode during LNT regeneration by maintaining the first switch closed and by maintaining the second switch in the first position.

At 516, method 500 includes determining if the exhaust NOx load on the LNT has dropped below a threshold, NOx_Thr. The threshold may be a lower threshold of NOx load at which regeneration of the LNT may be terminated. The controller may measure the NOx load using various models, timers and sensors. If the exhaust NOx load has decreased below the threshold NOx_Thr, then method proceeds to 520 where LNT regeneration may be terminated. Typically, the LNT returns to NOx collection, the fuel injection rates may be decreased to lean rates depending on the engine operating conditions. Method 500 then proceeds to 522, where the soot sensor electrodes may be re-connected based on the operating condition of the soot sensor. For example, the soot sensor may return to detecting particulate matter in the exhaust line, in which case, the soot sensor may be transitioned to particulate matter detection mode wherein the positive electrode may be reconnected to the positive voltage by closing the first switch and the negative voltage may be reconnected to ground by shifting the second switch from the third to the first position. Method 500 then proceeds to 523, where the LNT regeneration history may be updated and the routine ends. For example, a duration elapsed between current regeneration routine and the immediately previous regeneration routine may be updated at 523.

However if the LNT regeneration conditions are not met, or the exhaust NOx load is not greater than Thr_NOx, when checked at 506, the method 500 proceeds to 508, where it may be determined if the exhaust SOx load on the LNT is greater than a threshold, Thr_deSOx, which is the threshold at which the LNT may be desulfated. The threshold may be the SOx load at which LNT is desulfated, for example. Alternately the threshold may be determined from the SOx or NOx adsorption rates or from the NOx signal, for example. As mentioned earlier, SOx competes with NOx for adsorption sites on the LNT. If the SOx load is not greater than Thr_deSOx, method 500 proceeds to 542, where the LNT may continue to collect exhaust NOx and SOx and the soot sensor may be operated in particulate matter detection mode and method 500 ends. However, if the SOx load on the LNT is greater than the threshold for desulfation the LNT may be desulfated. However, prior to initiation of desulfation (or during pre-desulfation) of the LNT, the soot sensor electrode circuitry may be adjusted to transition the soot sensor to a pre-desulfation mode at 509. During pre-desulfation, method 500 includes selectively disconnecting the positive electrode from the positive voltage by opening the first switch at 524. Subsequently, at 526 the negative electrode may be selectively connected to the positive voltage by shifting the three-way switch to the closed (second) position. Thus, in the pre-desulfation mode opening the first switch may electrically decouple the positive electrode from the positive voltage, and shifting the second switch to a second (closed) position may electrically couple the negative electrode to the positive voltage. The technical effect of connecting the negative electrode to the positive voltage is that the negative electrode of the soot sensor now derives a positive charge, and subsequently when desulfation of the LNT is initiated, both the positive and the negative electrode may possess positive charges and hence may be more resilient to $H_2S$ corrosion. The controller may maintain the soot sensor in pre-desulfation mode for a pre-determined threshold time (4 s, for example). At 527, the soot sensor electrodes may be transitioned from the pre-desulfation mode to the desulfation mode and LNT desulfation may be initiated. To explain further, at 528, the positive electrode may be maintained disconnected from the positive voltage. Furthermore, at 530 the negative electrode may be selectively disconnected from the positive voltage and left open by shifting the three-way switch to the third open position and at 532, LNT desulfation may be initiated. Desulfation requires elevated temperatures as well as reducing environment. The fuel injection rates may be alternated between rich and lean for a specified time. In one example, LNT may be subjected to five cycles of 10 s rich and 18 s lean mixture at temperatures in excess of 700° C. during desulfation.

At 534, method 500 includes determining if the SOx load on the LNT has dropped below a threshold, SOx_Thr. The threshold may be a lower threshold of SOx load at which desulfation of the LNT may be terminated. If the SOx load is not below the threshold SOx_Thr, then the LNT desulfation may be continued at 544. If SOx load drops below the threshold, then method proceeds to 536 where LNT desulfation may be terminated. The operation temperature of the LNT may be reduced, and the fuel injection rates may be returned to stoichiometric or lean rates depending on the engine operating conditions. Method 500 may proceed to 538, where the soot sensor electrodes may be readjusted based on the operating condition of the soot sensor. The soot sensor may transition from desulfation mode to particle detection mode in which case, the positive electrode may be reconnected to the positive voltage by closing the first switch and the negative electrode may be connected to ground by shifting the second switch from the third position to the first position. Method 500 then proceeds to 540, where the LNT desulfation history may be updated and the routine ends. For example, a frequency of LNT desulfation and/or an average duration between desulfations may be updated and the method ends.

In this way, the soot sensor electrode corrosion by $H_2S$ and $SO_2$ released during LNT desulfation may be reduced by performing the following during desulfation of LNT. Firstly, the positive electrode is disconnected from the positive voltage, and the negative voltage is connected to the positive voltage during pre-desulfation. Secondly, the positive electrode is maintained open and the negative electrode is disconnected from the positive voltage, during desulfation. Thus, when $H_2S$ is released during desulfation, both the electrode resemble disconnected positive potentials, hence the chances of sulfur based chemical reactions with the electrodes is reduced.

Turning now to FIG. 6, map 600 shows an example relationship between soot sensor electrode connections with respect to regeneration of LNT and desulfation of the LNT. Plots 602 and 604 show the position of the positive and negative electrode of the soot sensor during different sets of conditions. Plot 606 shows the conductance of the soot sensor during the corresponding conditions. Plots 608 and 610 show the respective exhaust NOx and exhaust SOx load on the LNT during the corresponding conditions. Plots 612 and 614 show the exhaust temperature and the air-fuel ratio during the corresponding conditions mentioned above. For each plot, time is depicted along the x (horizontal) axis while values of each respective parameter are depicted along the y (vertical) axis. It will be appreciated that the map 600 shows a shorter time scale.

During the time between $t_0$ and $t_1$, the soot sensor may be collecting particulates in the exhaust, i.e., being operated in the particulate matter detection mode, for example. During this first condition, the three-way switch connected to the negative electrode of the soot sensor may be in the first position as indicated by 602, and the two-way switch connected to the positive electrode may be in the closed position as indicated by 604. In this first condition, the positive electrode is electrically coupled to the positive voltage while the negative electrode is electrically coupled to ground via a measuring resistor as shown in FIG. 2. The soot sensor when positioned downstream of the DPF, may detect particles that are leaking through the DPF. When the DPF is functioning as expected, it filters out the particulates in the exhaust, hence the soot sensor positioned thus may not detect any particles. In the absence of soot particles between the electrodes, the conductance of the electrode pair is low as indicated by 606. However, during this time, assuming light load condition and engine operating at lean air-fuel ratio, as indicated by 614 and at exhaust temperature indicated by 612, the corresponding exhaust NOx and SOx accumulating on the LNT is shown by 608 and 610 respectively.

During lean conditions, the NOx is adsorbed at an accelerated rate as indicated by 608. At $t_1$, the NOx load on the LNT may reach the threshold load for LNT regeneration Thr_NOx indicated by 616. At $t_1$, LNT regeneration may be initiated. During the time between $t_1$ and $t_2$ when LNT regeneration occurs, the soot sensor electrodes may be transitioned as indicated by 602 and 604. That is, the negative electrode may be decoupled from ground and the positive electrode, by operating the three-way switch in the third (open) position as indicated by 602. Additionally, the positive electrode may be disconnected from the positive voltage by operating the two-way switch in the open position as indicated by 604. During the time between $t_0$ and $t_1$ when the switches are operated as shown, the conductance may not be measured, as indicated by 606. In alternate examples, the soot sensor may be continued in particulate matter detection mode, where the positive electrode switch may be maintained closed (as indicated by dashed lines in 604) and the negative electrode may be maintained in the first position (as indicated by dashed lines in 602) and the conductance may continue to read a low value similar to the value measured prior to initiation of LNT regeneration. Regeneration of the LNT typically involves changing the fuel injection rate to make the exhaust rich as indicated by 614. Once the exhaust NOx load on the LNT falls below a threshold, the LNT regeneration may be terminated, by increasing the fuel injection rate to lean rates as indicated by 614. Additionally the soot sensor may be transitioned from regeneration mode to particulate matter detection mode or maintained in particulate matter detection mode. That is, the first switch may be closed (or maintained closed) to electrically couple the positive electrode to the positive voltage and the second switch may be shifted from the third position to the first position (or maintained in the first position) to electrically couple the negative electrode to ground, as shown by 604 and 602. Typically, the NOx absorption may be carried out for 60 s and the regeneration may be carried out for 5 s, for example. A single NOx absorption and desorption (or LNT regeneration) cycle is shown between $t_0$ and $t_2$. The LNT may undergo several NOx absorption and regeneration cycles (another such cycle is shown between $t_2$ and $t_4$, for example). However, the SOx load on the LNT may be accumulated more slowly compared to the NOx accumulation on the LNT.

Turning now to FIG. 7, map 700 shows an example relationship between soot sensor electrode connections with respect to regeneration of LNT and desulfation of the LNT in a longer time scale. Plots 702 and 704 show the position of the positive and negative electrode of the soot sensor during different sets of conditions. Plot 706 shows the conductance of the soot sensor during the corresponding conditions. Plots 708 and 710 show the respective exhaust NOx and exhaust SOx load on the LNT during the corresponding conditions. Plots 712 and 714 show the exhaust temperature and the air-fuel ratio during the corresponding conditions mentioned above. For each plot, time is depicted along the x (horizontal) axis while values of each respective parameter are depicted along the y (vertical) axis. It will be appreciated that the map 700 shows a longer time scale.

Between $t_0$ and $t_{12}$, several NOx absorption and desorption cycles as explained in FIG. 6 are shown and the LNT may continue to adsorb SOx. During these cycles, the soot sensor may be operated in particulate matter detection mode as explained earlier. The positive electrode switch is closed and the negative electrode switch is in first position as shown by 704 and 702 respectively. In alternate examples, soot sensor may be operated in regeneration mode as described in FIG. 6. As explained earlier, engine exhaust contains oxides of sulfur (SOx), derived from fuel and lubricating oil, which compete with NOx for LNT adsorption sites and SOx is preferentially adsorbed over NOx and forms stable sulfates with the LNT storage materials. Depending on the fuel sulfur content, the time taken to load the LNT with SOx may be longer (15 minutes, for example). When the SOx load reaches the threshold Thr_deSOx at time $t_{12}$, the LNT may be desulfated. However, prior to initiating LNT desulfation routine, between time $t_{12}$ and $t_{13}$ the LNT may be operated in the pre-desulfation mode where the soot sensor electrodes may be operated in a second condition. During the second condition, the two-way switch coupling the positive electrode to the positive voltage may be opened to electrically decouple the positive electrode from the positive voltage as indicated by 704, while shifting the three-way switch coupling the negative electrode to the second position (indicated by 702) thereby electrically coupling the negative electrode to the positive voltage. The soot sensor is maintained in this pre-desulfation mode until desulfation is initiated at $t_{13}$. At $t_{13}$, the soot sensor electrodes may be operated in a third condition. In the third condition, the two-way switch is maintained open to electrically decouple the positive electrode from the positive voltage, while the second switch is transitioned to from the second to the third position to electrically decouple the negative electrode from both the positive voltage and ground as indicated by 704 and 702. During desulfation of the LNT between $t_{13}$ and $t_{14}$, the LNT catalyst may be periodically subjected to rich and lean cycles as indicated by 714 at elevated temperatures (700° C. for example) as indicated by 712. During this time, the SOx adsorption on the LNT gradually decreases, as shown by 710. During desulfation of the LNT, sulfur in the LNT is removed quickly, while generating lower amounts of $H_2S$ gas (generating mostly SO2 gas). However, any H2S that is released may not react with the charged soot sensor electrodes thereby reducing damage to the electrodes. Depending on the location of the soot sensor in the exhaust line, the elevated temperatures during desulfation may regenerate the soot sensor and the DPF. Thus during the time between $t_{13}$ and $t_{14}$ when the LNT is desulfated, the conductance between the soot electrodes may not be measured, as indicated by 706. Additionally, the soot sensor electrodes may be cleaned by operating the sensor heater during this time. At $t_{14}$, the desulfation routine may be terminated once the SOx load reached the threshold SOx_Thr. In addition, the soot sensor electrodes may be cooled and may be transitioned back to particulate matter detection mode by closing the first switch and shifting the second switch to position 1, for example. This may be carried out sequentially or concurrently or in reverse order. At $t_{14}$, the LNT may continue to accumulate NOx and SOx as shown by 708 and 710.

In one example, when the soot sensor is located downstream of the DPF, it may be used to diagnose any leaks in the DPF. At time $t_{15}$ s, there may be a leak in the DPF and consequently, there may be an increase in conductance of the soot sensor as shown by 706 as the soot sensor may be detecting the soot leaking from the DPF. When the conductance reaches a threshold Thr_soot, the soot sensor may be regenerated. During soot sensor regeneration, the positive electrode may be disconnected from the positive voltage by opening the two-way switch as indicated by 704, and the negative electrode may be disconnected from both the positive voltage and the ground by shifting the three-way switch to the third position as indicated by 702. In addition, the exhaust temperature may be increased as indicated by 712. In some examples, the exhaust temperature may not be increased, instead a heater may be used to regenerate the soot sensor. The controller may update the soot sensor regeneration history and the DPF percentage efficiency may be calculated as described earlier.

Thus, in response to the SOx load being higher than the threshold, the LNT is operated first in the pre-desulfation mode where the negative electrode is connected to the positive voltage for a brief duration, while the positive electrode is disconnected from the positive voltage. However, during desulfation, both the electrodes may be open, i.e. not connected to the positive voltage or ground, thereby reducing the possibility of sensor degradation. In this way, the sensor electrode corrosion in the presence of $H_2S$ may be reduced. By reducing soot sensor degradation, the percentage efficiency of the DPF may be measured reliably, and overall, false exhaust filter repairs and high warranty costs of replacing good DPF filters may be reduced, or conversely the risk of not detecting a failed DPF is reduced.

Thus, an example method, includes during a first condition, operating a first switch to electrically couple a positive electrode of a sensor to a positive voltage while operating a second switch to electrically couple a negative electrode of the sensor to ground. The method further includes during a second condition, operating the first switch to electrically decouple the positive electrode from the positive voltage while operating the second switch to electrically couple the negative electrode to the positive voltage. In addition, the method further includes during a third condition, operating the first switch to electrically decouple the positive electrode from the positive voltage while operating the second switch to electrically decouple the negative electrode from each of the positive voltage and the ground, where each of the first, second, and third conditions are mutually exclusive with one another. The first switch is a two-way switch and operating the first switch during the first condition includes closing the first switch and operating the first switch during the second condition includes opening the first switch, wherein the sensor is an interdigitated comb electrode soot sensor. The second switch is a three-way switch and operating the second switch during the first condition includes shifting the switch to a first position, operating the second switch during the second condition includes shifting the switch to a second position, and operating the second switch during the third condition includes shifting the switch to a third position. The third position may be in between the first and second positions. The first condition further includes a soot load of the sensor being lower than a threshold soot load, and a NOx load of a lean NOx trap (LNT) coupled upstream of the soot sensor deviating from a threshold NOx load, wherein deviating includes NOx load being higher or lower than the threshold NOx load. The second condition includes a SOx load of the LNT being higher than a threshold SOx load and a pre-condition for the third condition, and the third condition includes the soot of the sensor being higher than the threshold soot load, the NOx load of the LNT being higher than the threshold NOx load, and the SOx load of the LNT being higher than the threshold SOx load and a deSOx mode.

In one example, an engine exhaust system, comprises an engine including an exhaust passage, a lean NOx trap (LNT), an exhaust filter DPF, a soot sensor coupled downstream of each of the LNT and DPF, the soot sensor including a first positive comb electrode interdigitated with a second negative comb electrode, the first electrode coupled to a positive voltage via a first switch, the second electrode coupled to ground via each of a measuring resistor and a second switch. The controller with computer-readable instructions stored on non-transitory memory may be configured for operating the exhaust system in a first mode with the first switch closed to electrically couple the positive electrode to the positive voltage, and the second switch in a first position to electrically couple the negative electrode to the ground. The controller may be further configured for operating the exhaust system in a second mode with the first switch open to electrically decouple the positive electrode from the positive voltage, and the second switch in a second position to electrically couple the negative electrode to the positive voltage. The controller may be further configured for operating the exhaust system in a third mode with the first switch open to electrically decouple the positive electrode from the positive voltage, and the second switch in a third position to electrically decouple the negative electrode from both the positive voltage and the ground. The controller may operate in the first mode responsive to a soot load of the sensor falling below a threshold soot load and a NOx load of the deviating from a threshold NOx load. Deviating from threshold further includes NOx load on the LNT being higher or lower than the threshold NOx load. The controller may further transition from the first mode to the second mode responsive to a SOx load of the LNT rising above a threshold SOx load and further transition from the first mode to the third mode responsive to the soot load of the sensor rising above the threshold soot load and the NOx load of the LNT being higher than the threshold NOx load. The controller may further transition from the second mode to the third mode responsive to the SOX load of the LNT staying above the threshold SOx load and further transition from the third mode to the first mode responsive to the soot load of the sensor falling below the threshold soot load and the NOx load of the LNT falling below the threshold NOx load and further transition from the third mode to the first mode responsive to the SOX load of the LNT falling below the lower threshold SOx load. The first switch is a two-way switch and the second switch is a three-way switch. A third position of the three-way switch may be located in-between the first and second positions.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types and to any exhaust where NOx and PM are removed and $H_2S$ can occur. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:
1. A method, comprising:
   selectively connecting and disconnecting a positive electrode of interdigitated comb electrodes of a sensor to and from a positive voltage; and
   selectively connecting a negative electrode of the interdigitated comb electrodes of the sensor to ground via a measuring resistor,
   wherein the sensor is a soot sensor coupled downstream of a lean NOx trap (LNT) in an exhaust system, and wherein the selectively connecting the positive elec- trode to the positive voltage is in response to any of the soot sensor being operated in a particulate matter detection mode and the LNT being operated in a regeneration mode.

2. The method of claim 1, wherein the selectively disconnecting the positive electrode from the positive voltage is performed in response to any of the soot sensor being operated in a regeneration mode, the LNT being operated in the regeneration mode, the LNT being operated in a pre-desulfation mode, and the LNT being operated in a desulfation mode.

3. The method of claim 1, wherein the positive electrode is electrically coupled to the positive voltage via a two-way switch, and wherein selectively connecting the positive electrode to the positive voltage includes closing the two-way switch, and selectively disconnecting the positive electrode from the positive voltage includes opening the two-way switch.

4. The method of claim 1, wherein the selectively connecting the negative electrode to the ground is in response to any of the soot sensor being operated in the particulate matter detection mode and the LNT being operated in the regeneration mode.

5. The method of claim 4, further comprising selectively connecting the negative electrode to the positive voltage in response to the LNT being operated in a pre-desulfation mode.

6. The method of claim 5, further comprising selectively disconnecting the negative electrode from each of the positive voltage and the ground in response to one of the soot sensor being operated in a regeneration mode, the LNT being operated in the regeneration mode, and the LNT being operated in a desulfation mode.

7. The method of claim 6, wherein the negative electrode is electrically coupled to the ground via a three-way switch, and wherein selectively connecting the negative electrode to ground includes shifting the three-way switch to a first position, selectively connecting the negative electrode to the positive voltage includes shifting the three-way switch to a second position, and selectively disconnecting the negative electrode from each of the ground and the positive voltage includes shifting the three-way switch to a third position.

8. The method of claim 7, wherein the particulate matter detection mode includes collecting of exhaust particulates on the soot sensor, wherein the pre-desulfation mode includes engine operation prior to desulfation of the LNT while a SOx load of the LNT is above a threshold SOx load, the regeneration mode includes one of regenerating the LNT responsive to a NOx load of the LNT being higher than a threshold NOx load, and regenerating the soot sensor responsive to a soot load of the sensor being higher than a threshold soot load, and wherein the desulfation mode includes desulfating the LNT responsive to the SOx load of the LNT being higher than the threshold SOx load.

9. A method, comprising:
during a first condition, operating a first switch to electrically couple a positive electrode of a sensor to a positive voltage while operating a second switch to electrically couple a negative electrode of the sensor to ground via a measuring resistor; and
during a second condition, operating the first switch to electrically decouple the positive electrode from the positive voltage while operating the second switch to electrically couple the negative electrode to the positive voltage,
wherein the positive electrode and the negative electrode are interdigitated electrodes of an interdigitated comb soot sensor.

10. The method of claim 9, further comprising, during a third condition, operating the first switch to electrically decouple the positive electrode from the positive voltage while operating the second switch to electrically decouple the negative electrode from each of the positive voltage and the ground, where each of the first, second, and third conditions are mutually exclusive with one another.

11. The method of claim 10, wherein the first switch is a two-way switch and operating the first switch during the first condition includes closing the first switch and operating the first switch during the second condition includes opening the first switch.

12. The method of claim 11, wherein the second switch is a three-way switch and operating the second switch during the first condition includes shifting the switch to a first position, operating the second switch during the second condition includes shifting the switch to a second position, and operating the second switch during the third condition includes shifting the switch to a third position.

13. The method of claim 10, wherein the first condition includes a soot load of the sensor being lower than a threshold soot load, and a NOx load of a lean NOx trap (LNT) coupled upstream of the sensor deviating from a threshold NOx load, wherein the second condition includes a SOx load of the LNT being higher than a threshold SOx load and in preparation for desulfation of the LNT, and wherein the third condition includes the soot load of the sensor being higher than the threshold soot load, the NOx load of the LNT being higher than the threshold NOx load, and the SOx load of the LNT being higher than the threshold SOx load during a desulfation mode.

14. An engine exhaust system, comprising:
an engine including an exhaust passage;
a lean NOx trap (LNT);
a diesel particulate filter (DPF);
a soot sensor coupled downstream of each of the LNT and the DPF, the soot sensor including a first positive comb electrode interdigitated with a second negative comb electrode, the first positive electrode coupled to a positive voltage via a first switch, the second negative electrode coupled to ground via each of a measuring resistor and a second switch; and
a controller with computer-readable instructions stored on non-transitory memory for:
operating the exhaust system in a first mode with the first switch closed to electrically couple the first positive electrode to the positive voltage, and the second switch in a first position to electrically couple the second negative electrode to the ground via a measuring resistor;
operating the exhaust system in a second mode with the first switch open to electrically decouple the first positive electrode from the positive voltage, and the second switch in a second position to electrically couple the second negative electrode to the positive voltage; and
operating the exhaust system in a third mode with the first switch open to electrically decouple the first positive electrode from the positive voltage, and the second switch in a third position to electrically decouple the second negative electrode from both the positive voltage and the ground.

15. The system of claim 14, wherein the controller includes further instructions for:

operating in the first mode responsive to a soot load of the soot sensor falling below a threshold soot load and a NOx load of the LNT deviating from a threshold NOx load.

16. The system of claim 15, wherein the controller includes further instructions for:
transitioning from the first mode to the second mode responsive to a SOx load of the LNT rising above a threshold SOx load and in preparation for a desulfation of the LNT.

17. The system of claim 16, wherein the controller includes further instructions for:
transitioning from the first mode to the third mode responsive to the soot load of the soot sensor rising above the threshold soot load and the NOx load of the LNT being higher than the threshold NOx load; and
transitioning from the second mode to the third mode responsive to the SOx load of the LNT rising above the threshold SOx load and in a desulfation mode.

18. The system of claim 17, wherein the controller includes further instructions for:
transitioning from the third mode to the first mode responsive to the soot load of the soot sensor falling below the threshold soot load and the NOx load of the LNT falling below the threshold NOx load; and
transitioning from the second mode to the first mode responsive to the SOx load of the LNT falling below the threshold SOx load and leaving the desulfation mode.

19. The system of claim 14, wherein the first switch is a two-way switch and wherein the second switch is a three-way switch.

* * * * *